US011639530B2

(12) United States Patent
Ko et al.

(10) Patent No.: US 11,639,530 B2
(45) Date of Patent: May 2, 2023

(54) CD133 RELATED TO ANTICANCER AGENT RESISTANCE IN COLON CANCER AND USE THEREOF

(71) Applicant: KOREA UNIVERSITY RESEARCH AND BUSINESS FOUNDATION, Seoul (KR)

(72) Inventors: Je Sang Ko, Seoul (KR); Min-Soo Kang, Gyeonggido (KR)

(73) Assignee: Korea University Research and Business Foundation, Seoul (KR)

( * ) Notice: Subject to any disclaimer, the term of this patent is extended or adjusted under 35 U.S.C. 154(b) by 244 days.

(21) Appl. No.: 16/848,273

(22) Filed: Apr. 14, 2020

(65) Prior Publication Data
US 2020/0325545 A1    Oct. 15, 2020

(30) Foreign Application Priority Data

Apr. 15, 2019 (KR) ........................ 10-2019-0043765

(51) Int. Cl.
| | |
|---|---|
| *C12N 15/113* | (2010.01) |
| *C12Q 1/6886* | (2018.01) |
| *A61K 48/00* | (2006.01) |
| *A61K 45/06* | (2006.01) |
| *C12N 5/00* | (2006.01) |

(52) U.S. Cl.
CPC ............ *C12Q 1/6886* (2013.01); *A61K 48/00* (2013.01); *C12N 15/113* (2013.01); *A61K 45/06* (2013.01); *C12N 5/0006* (2013.01); *C12Q 2600/158* (2013.01)

(58) Field of Classification Search
None
See application file for complete search history.

(56) References Cited

U.S. PATENT DOCUMENTS

2010/0040637 A1* 2/2010 Van Orden ........ C07K 16/2896
435/375

OTHER PUBLICATIONS

Grunt et al. Am J Cancer Res 5:560-574 (Year: 2015).*
Minsoo Kang, et al., "Roles of CD133 in microvesicle formation and oncoprotein trafficking in colon cancer", The FASEB Journal, Mar. 2019, pp. 4248-4260, vol. 33.
Sherie L. Morrison, "Chimeric human antibody molecules: Mouse antigen-binding domains with human constant region domains", Proc. Natl., Acad. Sci., Immunology, Nov. 1984, pp. 6851-6855, vol. 81.
Christos S. Karapetis, M.D., et al., "K-ras Mutations and Benefit from Cetuximab in Advanced Colorectal Cancer", The New England Journal of Medicine, Oct. 23, 2008, pp. 1757-1765, vol. 359, No. 17.
F Loupakis, et al., "KRAS codon 61, 146 and BRAF mutations predict resistance to cetuximab plus irinotecan in KRAS codon 12 and 13 wild-type metastatic colorectal cancer", British Journal of Cancer, 2009, pp. 715-721, vol. 101.
Astrid Lievre, et al., "KRAS Mutation Status is Predictive of Response to Cetuximab Therapy in Colorectal Cancer", Cancer Research, Apr. 15, 2006, pp. 3992-3995, vol. 66, No. 8.
Federica Di Nicolantonio, et al., "Wild-Type BRAF is Required for Response to Panitumumab or Cetuximab in Metastic Colorectal Cancer", Journal of Clinical Oncology, Dec. 10, 2008, pp. 5705-5712, vol. 26, No. 35.
Rafael G. Amado, et al., "Wild-Type KRAS is Required for Panitumumab Efficacy in Patients With Metastatic Colorectal Cancer", Journal of Clinical Oncology, Apr. 1, 2008, pp. 1626-1634, vol. 26, No. 10.

* cited by examiner

*Primary Examiner* — Brian Whiteman
(74) *Attorney, Agent, or Firm* — Sughrue Mion, PLLC

(57) ABSTRACT

The present invention relates to a use of CD133 involved in resistance to an EGFR-targeting agent in colon cancer. The CD133 protein may be used as a novel target protein for diagnosing and treating resistant cancer as well as general cancer.

1 Claim, 14 Drawing Sheets

Specification includes a Sequence Listing.

[FIG 1A]
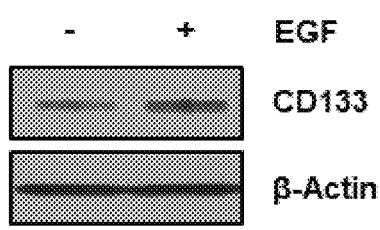
[FIG 1B]
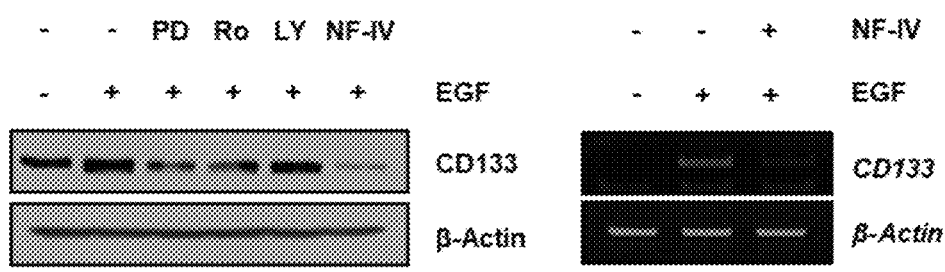

[FIG 1C]
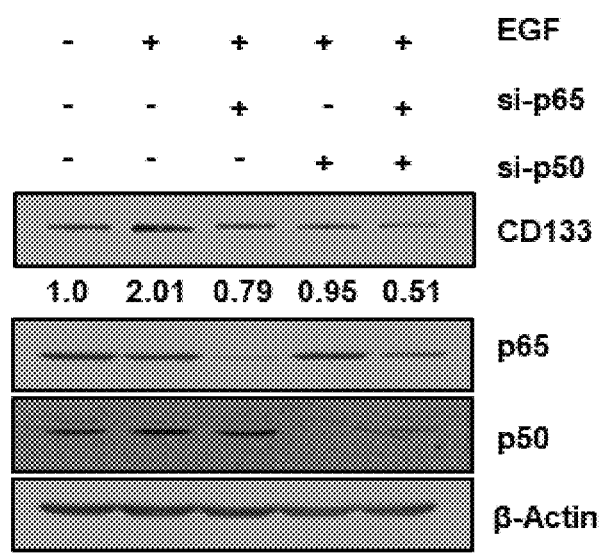
[FIG 1D]
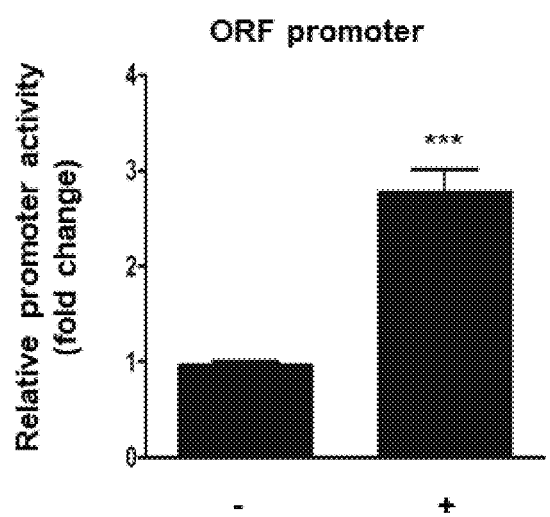

[FIG 1E]
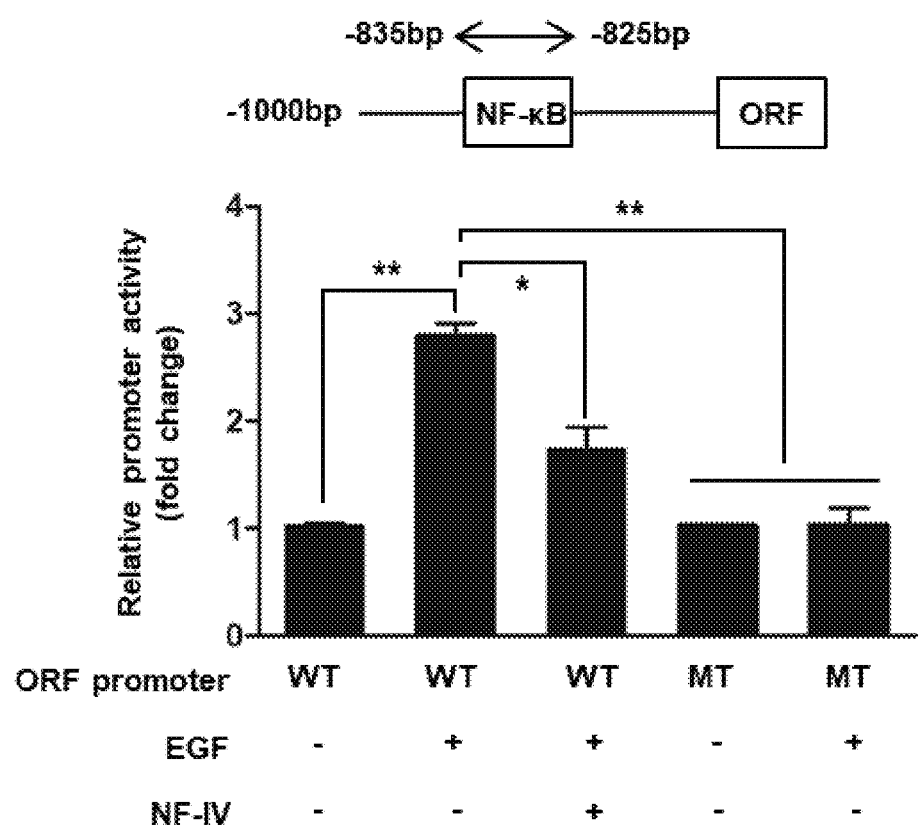

[FIG 2A]
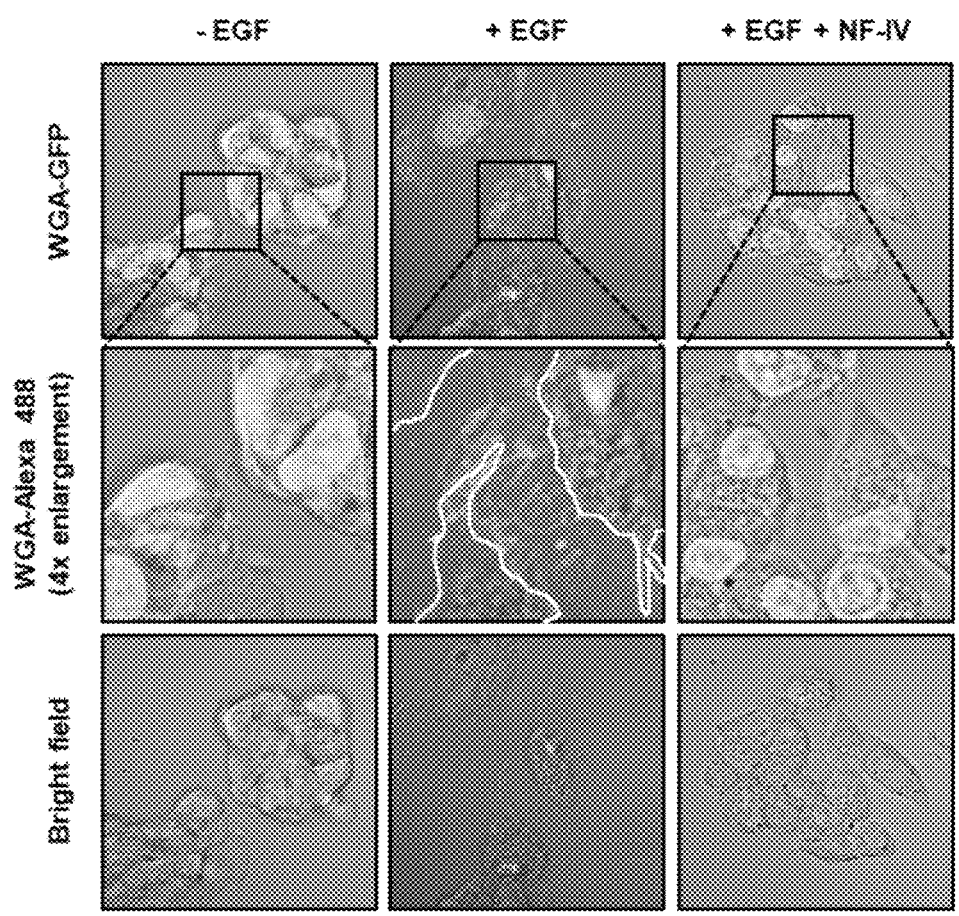

[FIG 2B]
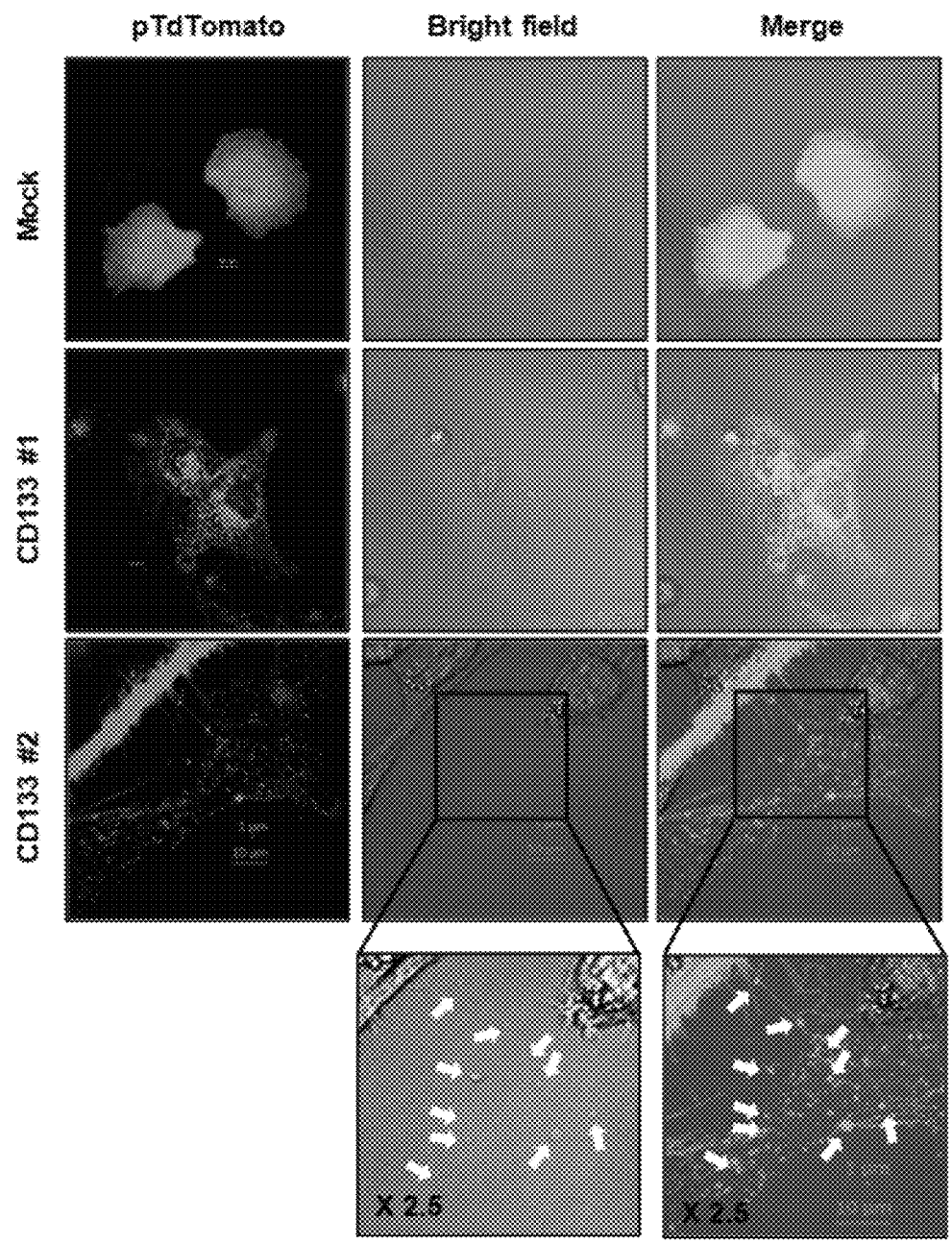

[FIG 2E]
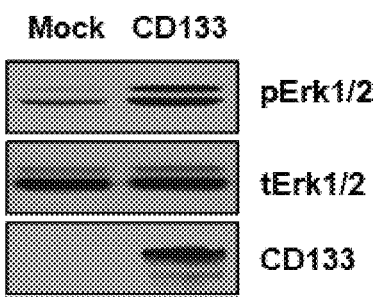
[FIG 3A]
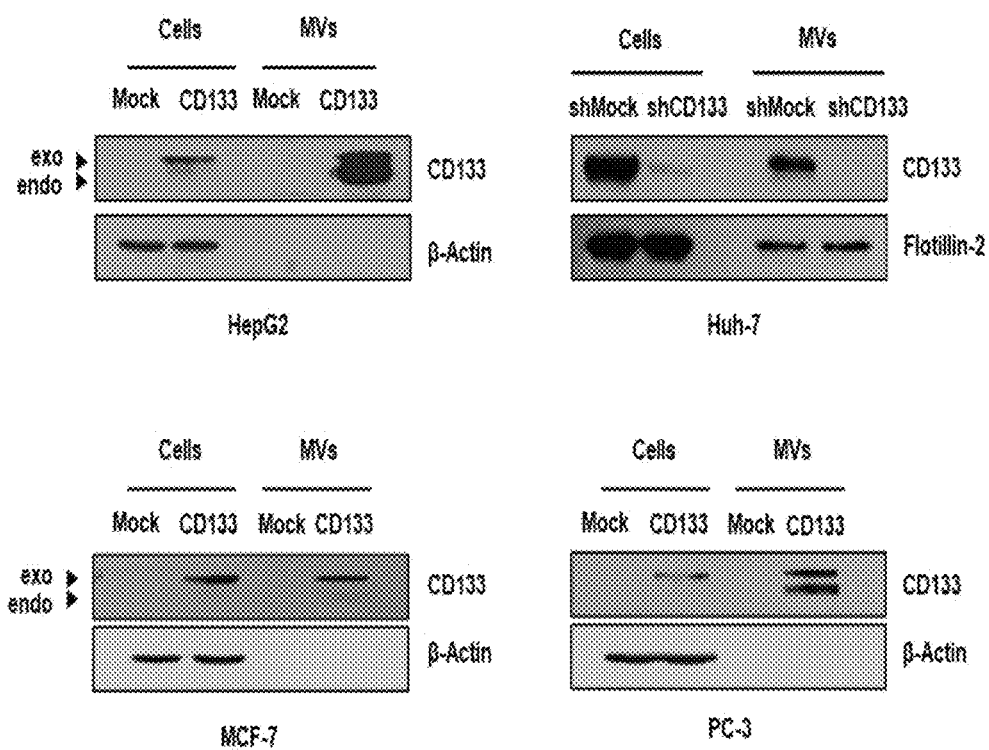

[FIG 3B]
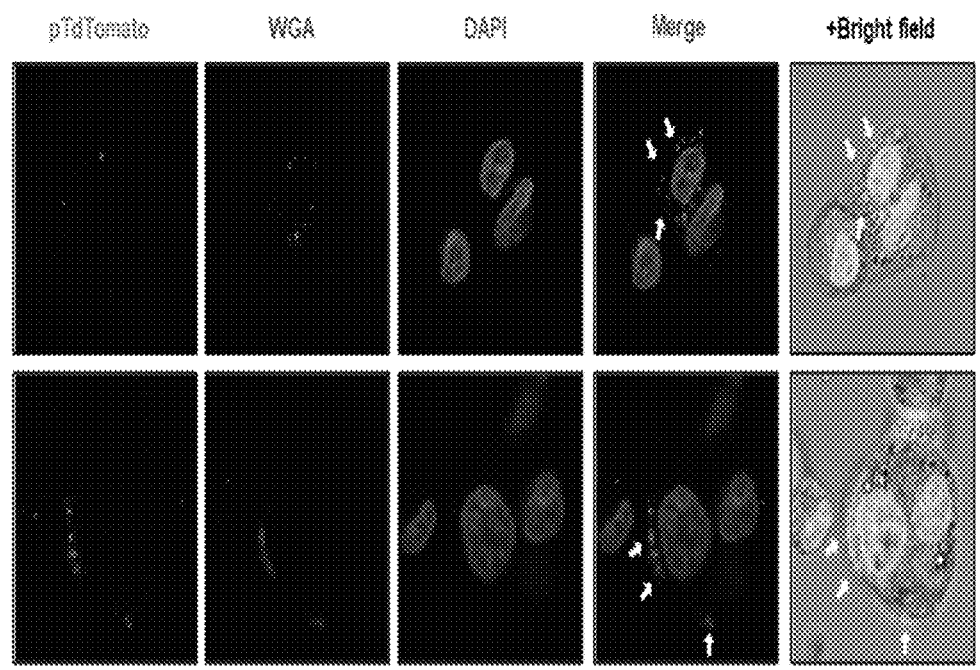

[FIG 4A]
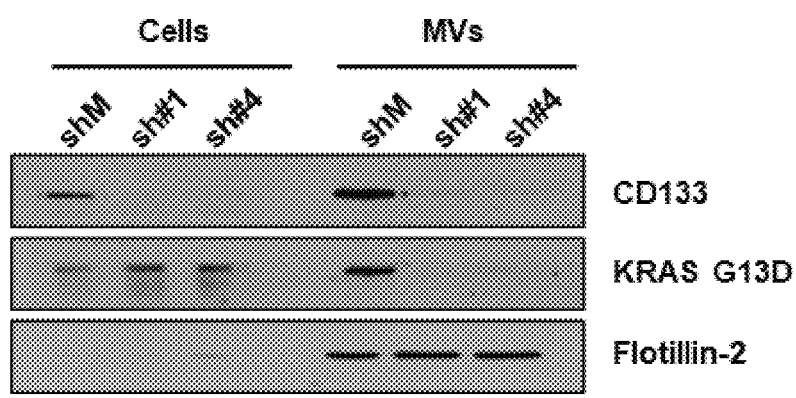
[FIG 4B]
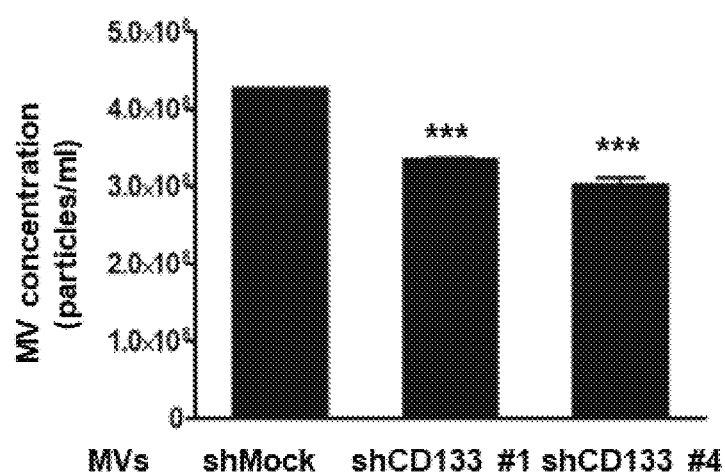

[FIG 4C]
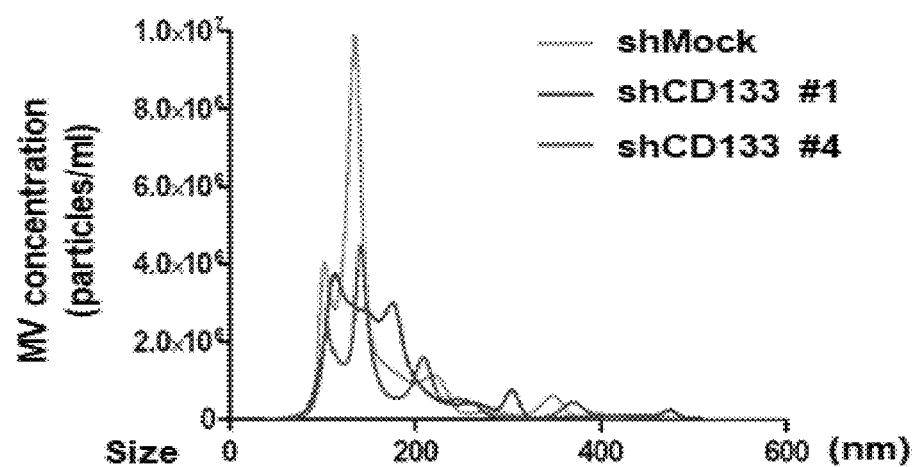
[FIG 4D]
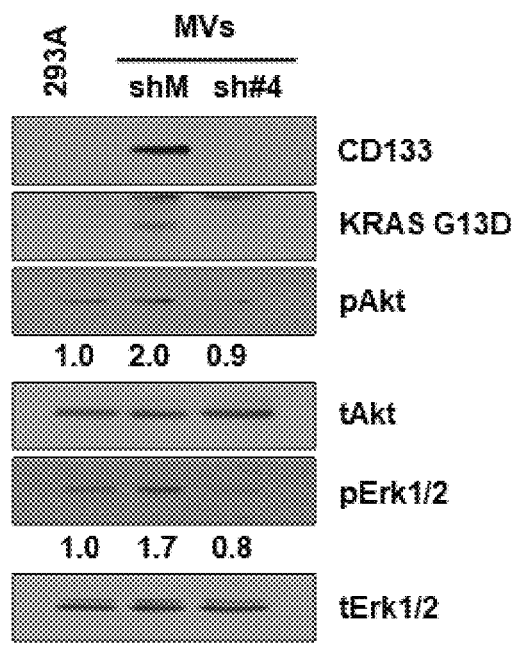

[FIG 4E]
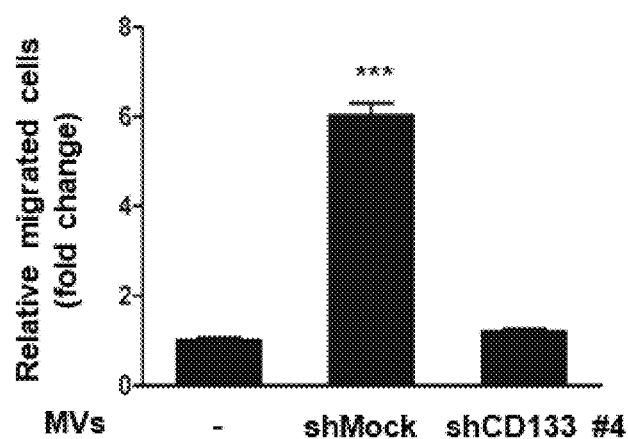
[FIG 4F]
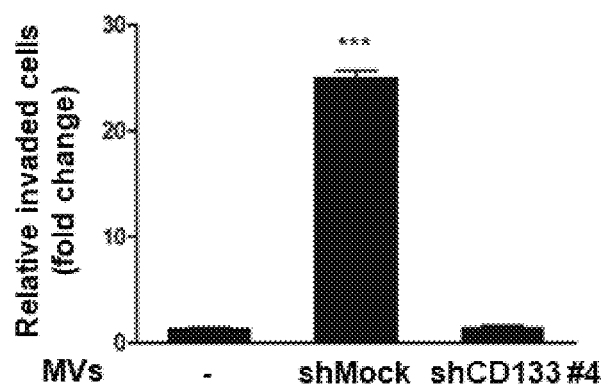

[FIG 5A]
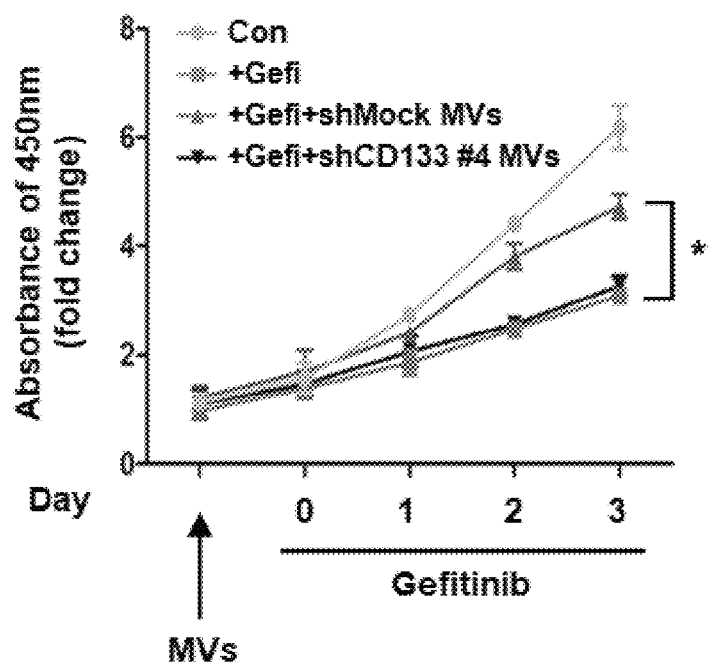
[FIG 5B]
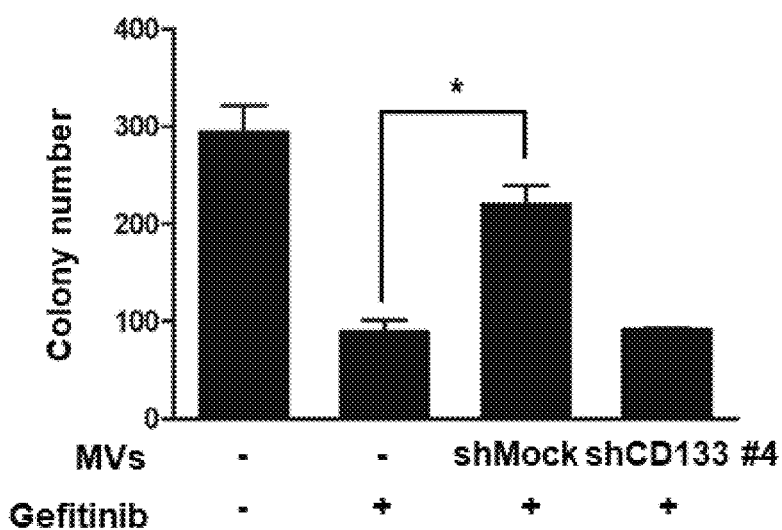

[FIG 5C]
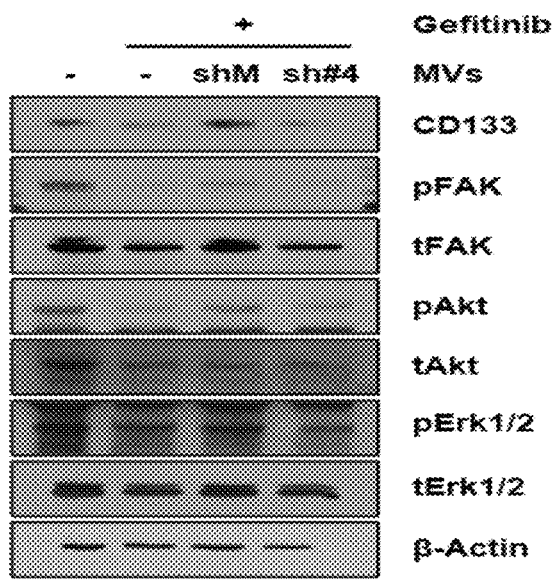
[FIG 5D]
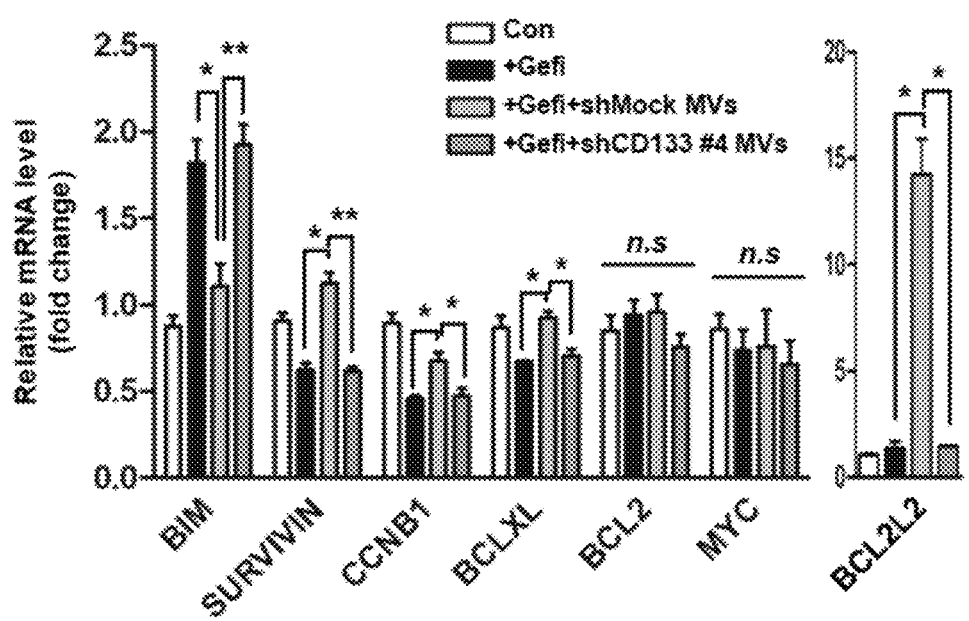

[FIG 5E]
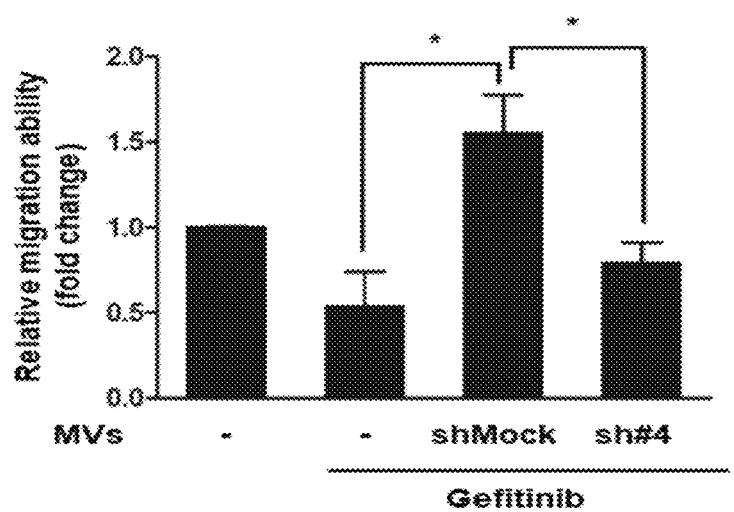
[FIG 5F]
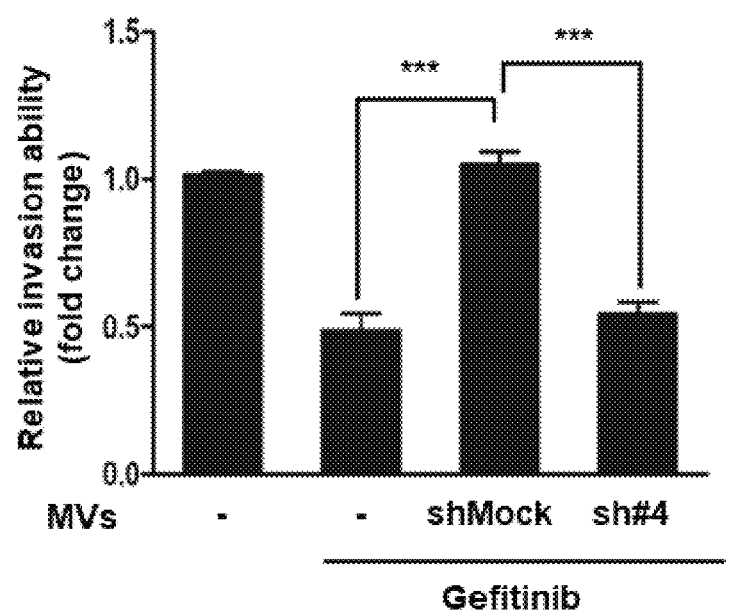

CD133 RELATED TO ANTICANCER AGENT RESISTANCE IN COLON CANCER AND USE THEREOF

INCORPORATION BY REFERENCE OF SEQUENCE LISTING

The content of the electronically submitted sequence listing, file name: Q254652sequencelistingasfiled.txt; size: 11,349 bytes; and date of creation: Apr. 14, 2020, is hereby incorporated by reference in their entirety.

TECHNICAL FIELD

The present invention relates to a use of CD133 involved in anticancer agent resistance in colon cancer.

BACKGROUND ART

Although many anticancer agents against various types of cancer have been developed to date, only a few types of cancer can be completely cured with an anticancer agent alone, this is because cancer cells do not respond to an anticancer agent in cancer treatment with the anticancer agent, or tumors are effectively reduced in an early stage, but develop anticancer agent resistance during or after treatment. Therefore, for effective anticancer treatment, resistance to an anticancer agent, for example, anticancer agent resistance of cancer cells, has to be overcome.

Generally, a mutation in the KRAS, NRAS or BRAF gene results in production of a protein having a modified signaling characteristic in tumor cells, and such a mutation has been known to be associated with unsuccessful results in cancer treatment using a therapeutic antibody targeting an epithelial growth factor receptor (EGFR), for example, gefitinib, cetuximab or panitumumab (Amado, Wolf et al. 2008; Karapetis, Khambata-Ford et al. 2008; Di Nicolantonio, Martini et al. 2008; Loupakis, Ruzzo et al. 2009; Lievre, Bachet et al. 2006). For example, KRAS G13D known as a colon cancer mutant cell line was reported to have resistance (tolerance) to an anticancer agent targeting EGFR.

For this reason, to improve a therapeutic effect of an anticancer agent targeting EGFR for cancer treatment, it is urgent to solve such a problem of anticancer agent resistance. Research on the identification of a specific cause or mechanism of the anticancer agent resistance has been persistently conducted, but it is a reality that little is known about it.

Nevertheless, the inventors had identified that, through a resistance study for colon cancer mutant cell lines resistant to an anticancer agent targeting EGFR, CD133 is related to resistance of colon cancer cells against an anticancer agent targeting EGFR, and thus the present invention was completed.

Technical Problem

The present invention is directed to providing a biomarker composition for diagnosing resistance to an EGFR-targeting agent in colon cancer, which includes CD133 protein or a gene encoding the same.

The present invention is also directed to providing a kit for diagnosing resistance to an EGFR-targeting agent in colon cancer.

The present invention is also directed to providing a method of providing information required for diagnosis of resistance to an EGFR-targeting agent in colon cancer.

Technical Solution

The inventors had confirmed, through a study on a KRAS G13D mutant colon cancer cell line having resistance to an EGFR-targeting agent, that the cell migration to and invasiveness of adjacent normal cells are highly improved by transferring the mutant to adjacent cells via microvesicles, the migration of KRAS G13D via microvesicles imparts anticancer agent resistance to adjacent colon cancer cells, and the CD133 protein controlling the release of microvesicles is related to resistance to an EGFR-targeting agent, and thus the present invention was completed.

The present invention is characterized by confirming whether colon cancer cells have resistance to an EGFR-targeting agent using the activity of the CD133 gene and an active protein, which is a product thereof, as a biomarker.

To this end, the present invention provides a biomarker composition for diagnosing resistance to an EGFR-targeting agent in colon cancer, which includes the CD133 protein or a gene encoding the same.

The biomarker of the present invention may be a marker with anticancer agent resistance, which is an EGFR-targeting agent, and since it has excellent accuracy and reliability as a marker for diagnosing anticancer agent resistance, the biomarker may be used to diagnose the occurrence, development and/or metastasis of resistant cancer, and treat resistant cancer.

The term "resistance" or "tolerance" used herein means that an organism does not sensitively respond to a drug, and thus withstands the drug's effects.

CD133 used as a biomarker for resistance diagnosis in the present invention is one of the representative CD-type proteins expressed on the surface of cancer stem cells, which are reported to be mainly present in cancer stem cells of colon cancer, liver cancer, pancreatic cancer and lung cancer.

The term "colon cancer" used herein is a collective term referring to rectal cancer, colorectal cancer and anal cancer.

In addition, the EGFR-targeting agent of the present invention refers to an anticancer agent, which may be any EGFR-targeting agent exhibiting an anticancer effect, and is used interchangeably with an EGFR-targeting drug. Preferably, the EGFR-targeting agent is one or more selected from the group consisting of cetuximab, gefitinib, erlotinib, panitumumab, PKI-166, EKB-569, HKI-272 (WAY-177820), icotinib, brigatinib, afatinib, lapatinib, canertinib, AEE788, XL647, and Zactima. More preferably, the EGFR-targeting agent is cetuximab, gefitinib, erlotinib or panitumumab, and most preferably, gefitinib.

The term "diagnosis" used herein refers to the detection of a pathological condition, which means, in terms of the purpose of the present invention, the determination of the presence or absence of resistance, and the development or alleviation of symptoms of a disease by examining the presence or absence of the expression of a biomarker for diagnosing resistance to an EGFR-targeting agent.

The "diagnosis biomarker" used herein refers to a material that can be used in diagnosis by distinguishing the presence or absence of resistance to an EGFR-targeting agent, and includes organic biomolecules such as polypeptides or nucleic acids (e.g., mRNA, etc.), lipids, glycolipids, glycoproteins, saccharides (a monosaccharide, a disaccharide, an oligosaccharide, etc.), which increase or decrease in cancer cells resistant to an anticancer agent, compared to cancer cells. The biomarker for resistance diagnosis according to the present invention may be a protein expressed from the CD133 gene whose expression level is increased in resistant cancer cells with respect to an EGFR-targeting agent, compared to general cancer cells.

The composition for diagnosing resistance to an EGFR-targeting agent may include an agent that measures an mRNA expression level of the CD133 gene or an amount of a protein expressed from the gene, and such an agent may be an oligonucleotide having a complementary sequence to CD133 mRNA, for example, a primer or nucleic acid probe specifically binding to CD133 mRNA, or an antibody specific for CD133 protein.

The primer refers to a single-stranded oligonucleotide that is able to serve as a starting point of template-directed DNA synthesis under suitable conditions (that is, four different types of nucleoside triphosphates and a polymerase) in a suitable buffer at a suitable temperature. A suitable length of the primer may vary according to various factors, for example, a temperature and the usage of the primer. In addition, the primer sequence is not required to be perfectly complementary to a partial sequence of the template, and it is sufficient that the primer sequence has sufficient complementarity within a range in which the primer can do an intrinsic action when hybridized with the template. Therefore, the primer of the present invention does not need to have a perfectly complementary sequence to the nucleotide sequence of a gene, which is the template, and it is reasonable that the primer has a sufficient complementarity within a range in which the primer can do an intrinsic action when hybridized with the gene sequence. In addition, the primer according to the present invention is preferably used in a gene amplification reaction. The amplification reaction refers to a reaction of amplifying a nucleic acid molecule, and amplification reactions of such a gene are well known in the art, and may include, for example, polymerase chain reaction (PCR), reverse transcriptase chain reaction (RT-PCR), ligase chain reaction (LCR), transcription-mediated amplification (TMA), and nucleic acid sequence-based amplification (NASBA).

The nucleic acid probe refers to a natural or modified monomer or linear oligomer consisting of linkages of such monomers, and includes a deoxyribonucleotide and a ribonucleotide, may be specifically hybridized with a target nucleotide sequence, and naturally occurs or is artificially synthesized. The probe according to the present invention may be a single chain, and preferably, an oligodeoxyribonucleotide. The probe of the present invention may include natural dNMPs (i.e., dAMP, dGMP, dCMP and dTMP), or nucleotide analogs or derivatives. In addition, the probe of the present invention may include a ribonucleotide. For example, the probe of the present invention may include backbone-modified nucleotides, such as a peptide nucleic acid (PNA), phosphorothioate DNA, phosphodithioate DNA, phosphoroamidate DNA, amide-linked DNA, MMI-linked DNA, 2'-O-methyl RNA, a-DNA and methyl phosphonate DNA; sugar-modified nucleotides, such as 2'-O-methyl RNA, 2'-fluoro RNA, 2'-amino RNA, 2'-O-alkyl DNA, 2'-O-allyl DNA, 2'-O-alkynyl DNA, hexose DNA, pyranosyl RNA and anhydrohexitol DNA; base-modified nucleotides, such as pyrimidines with a C-5 substituent (the substituent may be fluoro-, bromo-, chloro-, iodo-, methyl-, ethyl-, vinyl-, formyl-, ethynyl-, propynyl-, alkynyl-, thiazolyl-, imidazolyl-, or pyridyl-), 7-deazapurines with a C-7 substituent (the substituent may be fluoro-, bromo-, chloro-, iodo-, methyl-, ethyl-, vinyl-, formyl-, alkynyl-, alkenyl-, thiazolyl-, imidazolyl-, or pyridyl-); inosine; and diaminopurine.

The CD133-specific antibody may be a polyclonal antibody, a monoclonal antibody, a human antibody or a humanized antibody.

Examples of the antibody fragments include Fab, Fab', F(ab')$_2$ and Fv fragments; a diabody; a linear antibody (Zapata et al., Protein Eng. 8(10):1057-1062(1995)); a single-chain antibody molecule; and a multi-specific antibody formed from an antibody fragment.

When an antibody is digested with papain, two identical antigen-binding fragments, that is, "Fab" fragments having a single antigen-binding region, and the remainder, "Fc" fragment, are obtained. When treated with pepsin, a F(ab')$_2$ fragment which has two antigen-binding regions and is still able to be crosslinked to an antigen is produced. Fv is a minimal antibody fragment including a complete antigen-recognizing and binding region. This region consists of a dimer of one heavy chain variable region and one light chain variable region, which are firmly bound to each other by a non-covalent bond.

A method of preparing a polyclonal antibody is known to those of ordinary skill in the art. The polyclonal antibody may be prepared by one or more injections of an immunizing agent in combination with an immune adjuvant, if necessary, into a mammal. Generally, an immunizing agent and/or an immune adjuvant is/are subcutaneously or intraperitoneally injected into a mammal several times. The immunizing agent may be a protein of the present invention or a fusion protein thereof. It may be effective that an immunizing agent, as well as a protein known to be immunogenic, is injected into an immunized mammal.

The monoclonal antibody according to the present invention may be prepared by the hybridoma method disclosed in the literature (Kohler et al., Nature, 256:495 (1975)), or a recombinant DNA method (refer to U.S. Pat. No. 4,816,576). The monoclonal antibody may also be isolated from a phage antibody library using the technology disclosed in the literature (Clackson et al., Nature, 352:624-628 (1991) and Marks et al., J. Mol. Biol., 222:581-597 (1991)).

In the monoclonal antibody of the present invention, specifically, when exhibiting desired activity, a part of a heavy chain and/or a light chain is identical to or has homology with a corresponding sequence of an antibody derived from a specific species or an antibody belonging to a specific antibody class or subclass, whereas the remainder of the chain(s) includes an antibody derived from a different species, an antibody belonging to a different antibody class or subclass or a "chimeric" antibody which is identical or homologous to a fragment of such an antibody (Morrison et al., Proc. Natl. Acad. Sci. USA, 81:6851-6855 (1984)).

A "humanized" form of a non-human (e.g., rodents) antibody is a chimeric immunoglobulin including a minimal sequence derived from a non-human immunoglobulin, an immunoglobulin chain or a fragment thereof (e.g., Fv, Fab, Fab', F(ab')$_2$ or a different antigen-binding sequence of an antibody). In most cases, the humanized antibody includes a human immunoglobulin (recipient antibody) in which a complementarity-determining region (CDR) residue of a recipient is substituted with a CDR residue of a non-human species (donor antibody) such as a mouse, rat or rabbit, having desired specificity, affinity and ability. In some cases, aFv framework residue of the human immunoglobulin is substituted with a corresponding non-human residue. In addition, the humanized antibody may include a recipient antibody, or a residue which is not found in an introduced CDR or framework sequence. Generally, the humanized antibody substantially includes one or more, generally two or more variable domains, and here, all or substantially all CDR regions correspond to a region of a non-human immunoglobulin, and all or substantially all FR regions correspond to a region of a human immunoglobulin sequence. In addition, the humanized antibody includes at least a part of a variable region (Fc) of an immunoglobulin, generally, a part of a human immunoglobulin region (Presta, Curr. Op. Struct. Biol. 2:593-596 (1992)).

The composition for diagnosing resistance to an EGFR-targeting agent according to the present invention may be included in the form of a kit.

The kit may include a primer, probe or antibody which is able to measure the expression level of the CD133 gene or an amount of the CD133 protein, and the definition thereof is as described above.

When the kit is employed in PCR amplification, optionally, reagents required for PCR amplification, for example, a buffer, a DNA polymerase (e.g., a heat-stable DNA polymerase obtained from Thermusaquaticus (Taq), Thermusthermophilus (Tth), *Thermusfiliformis, Thermisflavus, Thermococcusliteralis* or *Pyrococcusfuriosus* (Pfu)), a DNA polymerase cofactor and dNTPs may be included, and when the kit is used in an immunoassay, the kit of the present invention may optionally include a secondary antibody and a marker substrate. Further, the kit according to the present invention may be manufactured in multiple individual packages or compartments containing the above-mentioned reagent components.

In addition, the composition for diagnosing resistance to an EGFR-targeting agent according to the present invention may be included in the form of a microarray.

In the microarray of the present invention, a primer, probe or antibody that is able to measure the expression level of the CD133 protein or gene encoding the same is used as a hybridizable array element, and fixed on a substrate. A preferable substrate may be a suitable rigid or semi-rigid support, for example, a membrane, a filter, a chip, a slide, a wafer, a fiber, a magnetic or non-magnetic bead, a gel, a tubing, a plate, a polymer, a microparticle and a capillary. The hybridizable array element may be arranged and immobilized on the substrate, and such immobilization may be performed by a chemical binding method or a covalent binding method such as UV. For example, the hybridizable array element may be bound to a glass surface which is modified to include an epoxy compound or an aldehyde group, or bound to a polylysine-coated surface using UV. In addition, the hybridizable array element may bind to a substrate by a linker (e.g., an ethylene glycol oligomer or a diamine).

Meanwhile, when a sample applied to the microarray of the present invention is a nucleic acid, it may be labeled and hybridized with an array element fixed on the microarray. Hybridization conditions may vary, and detection and analysis of a hybridization degree may be performed in various ways according to a labeling material.

In addition, the present invention provides a method of providing information for diagnosing resistance to an EGFR-targeting agent, which includes measuring the expression level of the CD133 gene or the expressed protein in a biological sample isolated from a patient, and more specifically, the method may include (a) measuring the expression level of the CD133 gene or an amount of the expressed protein in a biological sample of a patient; and (b) measuring the expression level of the gene and an amount of the expressed protein from a sample of a normal control and comparing it with the measurement result obtained in Step (a).

The method of measuring the expression level of a gene or an amount of a protein encoded by the gene may be performed by a known process of isolating mRNA or a protein from a biological sample using a known technique.

The biological sample refers to a sample obtained from the living body, which is different from a normal control in terms of the expression level of the gene or a protein level according to the occurrence or progression of resistance to an EGFR-targeting agent, and the sample may be, but is not limited to, tissue, a cell, blood, serum, plasma, saliva or urine.

The measurement of the expression level of a gene is preferably to measure an mRNA level, and methods of measuring an mRNA level include, but are not limited to, RT-PCR, real time reverse transcription polymerase chain reaction, RNase protection assay, Northern blotting and DNA chip assay.

The measurement of a protein level may use an antibody, and in this case, the CD133 protein in a biological sample and an antibody specific for the protein forms a binding product, that is, an antigen-antibody complex, and an amount of antigen-antibody complex formation may be quantitatively measured from the size of a signal of a detection label. The detection level may be selected from the group consisting of an enzyme, a fluorescent material, a ligand, a light-emitting material, a microparticle, a redox molecule and a radioisotope, but the present invention is not limited thereto. Analysis methods for measuring a protein level may include, but not limited to, Western blotting, ELISA, radioimmunoassay, radioimmunodiffusion, Ouchterlonyimmunodiffusion, rocket immunoelectrophoresis, immunohistochemical staining, immunoprecipitation assay, complement fixation assay, FACS, and protein chip assay.

Accordingly, the present invention may confirm mRNA expression levels or protein amounts in the control, a patient resistant to an EGFR-targeting agent, or a patient suspected of having resistance to an EGFR-targeting agent through the detection methods described above, and the expression levels are compared to be able to diagnose the occurrence and progression of the resistance to an EGFR-targeting agent.

In addition, according to the method of providing information for the diagnosis of the resistance to an EGFR-targeting agent according to the present invention, when the expression level of the CD133 gene according to the present invention or an amount of the expressed protein is higher than that of the normal control sample, it can be determined that a patient has resistance to an EGFR-targeting agent.

The present invention also relates to a composition for preventing or treating resistance to an EGFR-targeting agent, which includes a CD133 inhibitor.

The present invention also provides a use of a CD133 inhibitor for preparing a pharmaceutical composition for preventing or treating resistance to an EGFR-targeting agent.

According to the present invention, CD133 is highly expressed in cancer cells with resistance to an EGFR-targeting agent, as described above, and the expression of CD133 promotes budding of microvesicles, increases cell migration and invasiveness by delivering the oncogenic protein KRAS G13D to adjacent cells using microvesicles, and thus is involved in the occurrence of anticancer agent resistance.

Therefore, the CD133 inhibitor may be used in treatment of resistant cancer.

To this end, the composition for preventing or treating resistance to an EGFR-targeting agent of the present invention may include an agent for reducing mRNA expression of the CD133 gene or protein expression thereof, or degrading function or activity.

The CD133 protein inhibitor may be a peptide or compound which is bound with the CD133 protein to regulate a signal of a nerve differentiation pathway. The inhibitor may be selected by a screening method exemplified below, such as protein structure analysis, and may be designed using a method known in the art.

Specifically, the CD133 protein inhibitor may be a material which is bound with the CD133 protein consisting of an amino acid sequence represented by SEQ ID NO: 2 to inhibit activity.

In addition, as the protein inhibitor, a polyclonal antibody, monoclonal antibody, human antibody or humanized antibody against the CD133 protein may be used, and the definition of the antibody is as described above.

Resistant cancer may be prevented or treated by inhibiting the function of CD133 in cells using the antibody.

The functional or activity inhibitor of the CD133 protein according to the present invention may be delivered using a liposome, a virus, a gene gun, a polymer, ultrasonication or an electric shock, but the present invention is not particularly limited thereto.

The CD133 gene may be DNA encoding the same or mRNA transcribed therefrom. Accordingly, the inhibitor of the gene may be an inhibitor which is bound to the gene itself to interfere with transcription or bound to mRNA transcribed from the gene to interfere with the translation of mRNA.

Therefore, the inhibitor of the CD133 gene includes all types of inhibitors that inhibit the expression of the CD133 gene. For example, such an inhibitor may be a peptide, nucleic acid or compound binding to the gene. The inhibitor may be selected by a screening method to be described below, such as cell-based screening, and may be designed by a method known in the art.

In one embodiment, the inhibitor may be an antisense-oligonucleotide, siRNA, shRNA or miRNA against the CD133 gene or a vector including the same. Such an antisense-oligonucleotide, siRNA, shRNA, miRNA or a vector including the same may be manufactured using a method known in the art. Specifically, the inhibitor may be a nucleic acid molecule prepared to inhibit the expression of the CD133 gene consisting of SEQ ID NO: 1.

The term "siRNA" used herein refers to double-stranded RNA inducing RNA interference through the cleavage of mRNA of a target gene, and consists of an RNA strand of a sense sequence having the sequence like mRNA of the target gene and an RNA strand of an antisense sequence having a sequence complementary thereto.

The siRNA may include siRNA synthesized in vitro, or a form expressed by inserting a base sequence encoding siRNA into an expression vector.

The "vector" used herein refers to a gene construct including foreign DNA inserted into a genome encoding a polypeptide.

The vector related to the present invention is a vector in which a nucleic acid sequence inhibiting the gene is inserted into a genome, and such a vector may be a DNA vector, a plasmid vector, a cosmid vector, a bacteriophage vector, an enzyme vector, or a viral vector.

In addition, the antisense may have a sequence complementary to an entire or partial mRNA sequence transcribed from the CD133 gene or a fragment thereof, and bind to the mRNA to inhibit the expression of the CD133 gene or a fragment thereof.

In addition, the short hairpin RNAi (shRNAi) may be manufactured by a conventional method using a human or mouse shRNAi common base sequence region as a target.

In addition, the pharmaceutical composition of the present invention may further include a pharmaceutically acceptable carrier.

The pharmaceutically acceptable carrier includes a carrier and a vehicle, which are generally used in the pharmaceutical field, and specifically, includes an ion exchange resin, alumina, aluminum stearate, lecithin, a serum protein (e.g., human serum albumin), a buffer material (e.g., various types of phosphates, glycine, sorbic acid, potassium sorbate, or a partial glyceride compound of a saturated vegetable fatty acid), water, a salt or electrolyte (e.g., protamine sulfate, disodium hydrogen phosphate, potassium hydrogen phosphate, sodium chloride or a zinc salt), colloidal silica, magnesium trisilicate, polyvinylpyrrolidone, a cellulose-based substrate, polyethylene glycol, sodium carboxymethylcellulose, polyarylate, wax, polyethylene glycol or lanolin, but the present invention is not limited thereto.

In addition, the composition of the present invention may further include a lubricant, a wetting agent, an emulsifier, a suspending agent, or a preservative, other than the above-described components.

In one aspect, the composition according to the present invention may be prepared as an aqueous solution for parenteral administration, and preferably, a Hank's solution, a Ringer's solution or a buffer solution such as physically buffered saline is used. An aqueous injectable suspension may include a substrate that can increase the viscosity of the suspension such as sodium carboxymethylcellulose, sorbitol or dextran.

The composition of the present invention may be systemically or locally administered, and formulated in a suitable form by known technology for such administration. For example, for oral administration, the composition may be administered by mixing the active compound with an inactive diluent or edible carrier, encapsulating all components with a hard or soft gelatin capsule or compressing all components in the form of a tablet. For oral administration, the active compound may be mixed with an excipient, and then formed as an edible tablet, a buccal tablet, a troche, a capsule, an elixir, a suspension, a syrup or a wafer.

Various forms for injection or parenteral administration may be prepared according to a technique known or commonly used in the art. Since CD133 is well dissolved in saline or a buffer solution, after storage in a freeze-dried state, an effective amount of CD133 may be mixed in saline or a buffer solution to prepare a solution suitable for intravenous injection, subcutaneous injection, muscle injection, intraperitoneal injection or transdermal injection, right before the administration.

The effective amount of the active ingredient of the pharmaceutical composition of the present invention refers to an amount required for prevention, inhibition or alleviation of a disease.

Accordingly, the effective amount may be adjusted by various factors such as the type and severity of a disease, the type and content of the active ingredient and other components, contained in the composition, the type of a dosage form, and the age, body weight, general health condition, gender and diet of a patient, administration time, administration route, a release rate of the composition, a treatment period, and a co-used drug. While not limited thereto, for example, in the case of an adult, the inhibitor of the present invention may be administered once or several times a day, when the type of the inhibitor is a compound, it may be administered at a dose of 0.1 ng/kg to 10 g/kg, when the type of the inhibitor is a polypeptide, protein or antibody, it may be administered at a dose of 0.1 ng/kg to 10 g/kg, or when the type of the inhibitor is an antisense-oligonucleotide, siRNA, shRNAi or miRNA, it may be administered at a dose of 0.01 ng/kg to 10 g/kg.

The present invention also provides a method of treating an animal with resistance to an EGFR-targeting agent, which includes administering a composition including a pharmaceutically effective amount of a CD133 inhibitor for preventing or treating resistance to an EGFR-targeting agent to a subject.

A pharmaceutical composition and an administration method, which are used in the method of treating resistance to an EGFR-targeting agent, are as described above, and the common description between them will be omitted to avoid excessive complexity of the specification.

Meanwhile, subjects to which the pharmaceutical composition for preventing or treating resistance to an EGFR-targeting agent may be administered include all kinds of animals. For example, the subjects may be non-human animals such as dogs, cats, and mice.

The present invention also provides a method of screening a drug for preventing or treating resistance to an EGFR-targeting agent, which includes bringing the CD133 gene into contact with a candidate ex vivo, and determining whether the candidate promotes or inhibits the expression of the gene.

In addition, the present invention provides a method of screening a drug for preventing or treating resistance to an EGFR-targeting agent, which includes bringing the CD133 protein into contact with a candidate ex vivo, and determining whether the candidate improves or inhibits the function or activity of the protein.

According to the screening method of the present invention, first, a candidate to be analyzed may be brought into contact with resistant cancer cells having the gene or protein.

The candidate may be an individual nucleic acid, protein or peptide, another extract or natural substance, or a compound, which is expected or randomly selected to have a potential as a material promoting or inhibiting the mRNA transcription or mRNA translation into a protein in the base sequence of the CD133 gene or a drug improving or inhibiting the function or activity of the CD133 protein according to a common selection method.

Afterward, in cells treated with a candidate, the expression level of the gene or the amount or activity of the protein may be measured, and as a result of the measurement, when the expression level of the gene or the amount or activity of the protein is measured as increased or decreased, the candidate may be determined as a material for treating or preventing resistant cancer.

The method of measuring the expression level of the gene, or the amount or activity of the protein may be performed by various methods known in the art, and may be, for example, RT-PCR, real time-polymerase chain reaction, Western blotting, Northern blotting, ELISA, radioimmunoassay (RIA), radioimmunodiffusion and immunoprecipitation assay, but the present invention is not limited thereto.

The candidate exhibiting an activity of inhibiting gene expression or a protein function, obtained by the screening method of the present invention, may be a candidate for a resistant cancer therapeutic agent.

The candidate for a therapeutic agent against cancer resistant to an EGFR-targeting agent serves as a leading compound in the development of a therapeutic agent against resistance to an EGFR-targeting agent, and modifies and optimizes the structure of the leading compound to exhibit an effect of inhibiting the CD133 gene or the function of a protein expressed therefrom, thereby developing a novel therapeutic agent against cancer resistant to an EGFR-targeting agent.

Details related to genetic engineering technology in the present invention will become more apparent from the content disclosed in Sambrook, et al. Molecular Cloning, A Laboratory Manual, Cold Spring Harbor laboratory Press, Cold Spring Harbor, N.Y. (2001); and Frederick M. Ausubel et al., Current protocols in molecular biology volume 1, 2, 3, John Wiley & Sons, Inc. (1994).

Advantageous Effects

The present invention identifies that the CD133 protein expressed in colon cancer increases resistance to an EGFR-targeting agent, and thus the CD133 protein can be used as a novel target protein for diagnosing and treating resistant cancer as well as general cancer.

DESCRIPTION OF DRAWINGS

The patent or application file contains at least one drawing executed in color. Copies of this patent or patent application publication with color drawing(s) will be provided by the Office upon request and payment of the necessary fee.

FIGS. 1A-1E show the result of identifying a CD133 expression regulatory mechanism in liver cancer cells: (A) the change in CD133 expression according to EGF expression; (B-C) the change in CD133 expression according to an EGF downstream signaling molecule, NF-KB; and (D-E) the relationship between NF-κB and CD133, confirmed by promoter activity.

FIGS. 2A-2E show the result of confirming that CD133 is involved in promotion of microvesicle budding in liver cancer cells: (A) confirmation of the relationship between an EGF signaling system and microvesicle and TNT formation; (B) confirmation of microvesicle and TNT formation in a CD133-overexpressing cell line; and (C-E) confirmation of the change in activation of Rac1 and RhoA associated with microvesicle budding and a downstream signaling factor, Erk1/2, of RhoA according to CD133 expression FIGS. 3A-3B show the result of analyzing microvesicles budded from cancer cells: (A) the result of confirming whether CD133 is included in microvesicles budded from various cancer cells; and (B) the result of observing the migration of microvesicles containing CD133 to adjacent cells.

FIGS. 4A-4F show the result of confirming that CD133 is involved in oncogenic protein transport and microvesicle budding in colon cancer: (A) confirmation whether an oncogenic protein is contained in microvesicles according to CD133 expression; (B-C) confirmation that CD133 expression contributes to microvesicle budding and a size change; (D) confirmation that CD133 expression contributes to the transport of an oncogenic protein via microvesicles and cell proliferation; and (E-F) confirmation that the transport of an oncogenic protein via microvesicles contributes to the change in cell migration to and invasiveness of adjacent normal cells.

FIGS. 5A-5F show the result of confirming that CD133-containing microvesicles induce anticancer agent resistance (gefitinib) in colon cancer: (A-B) confirmation of the capability of CD133-containing microvesicles to induce anticancer agent resistance (gefitinib) by confirmation of the proliferation of cancer cells; (C-D) the result of confirming that cancer cell proliferation is caused by an oncogenic protein transported by microvesicles through the change in KRAS downstream signaling molecule and target gene expression; and (E-F) confirmation that cell migration to and invasiveness of adjacent normal cells are changed by the oncogenic protein transported by CD133-containing microvesicles in the presence of gefitinib.

MODES OF THE INVENTION

Figure 2C:
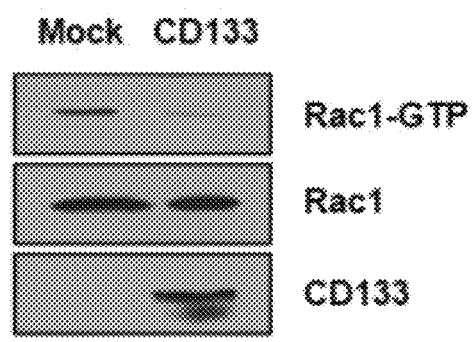
Figure 2D:
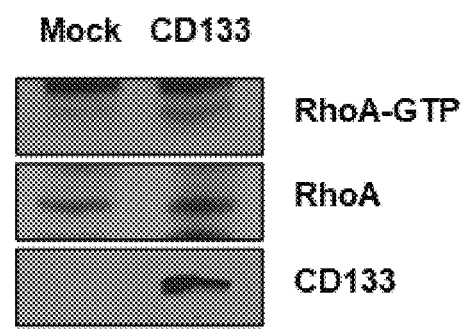

Hereinafter, the advantages and features of the present invention and the methods of accomplishing the same may be clearly understood with reference to the detailed description of exemplary embodiments and the accompanying drawings. However, the present invention is not limited to the exemplary embodiments disclosed below, and may be embodied in many different forms. These exemplary embodiments are merely provided to complete the disclosure of the present invention and fully convey the scope of the present invention to those of ordinary skill in the art, and the present invention should be defined by only the accompanying claims.

EXAMPLE 1

Confirmation of CD133 Expression Regulatory Mechanism in Cancer Cells

An epithelial growth factor (EGF) signaling system has been reported to be significant in the occurrence and development of cancer. CD133 (NCBI Gene ID: 8842) is known as a marker of a cancer stem cell, and particularly, to play a crucial role in formation of liver cancer stem cells. Therefore, the correlation between the EGF signaling system and CD133 expression in a liver cancer cell line was investigated.

After treatment with an inhibitor against an EGF downstream signaling molecule, CD133 expression was investigated. Specifically, for transfection and Western blotting, a specific gene (plasmid vector or siRNA) was expressed in cells using a transfection reagent. For general plasmid vector transfection, 24 hours after transfection, cells were harvested, and for siRNA transfection, 48 hours after transfection, cells were harvested. For Western blotting, the harvested cells were lysed in RIPA buffer, and centrifuged at 12,000 g for 20 minutes at 4° C., followed by collecting a supernatant. The collected supernatant was subjected to SDS-PAGE gel electrophoresis, and transferred onto a nitrocellulose membrane, followed by detecting the expression of a desired protein using suitable antibodies. As a result, it was observed that NF-κB is involved in EGF-induced CD133 expression (FIG. 1B). It was confirmed that, when the expression of NF-κB subunits, such as p50 (NCBI Gene ID: 4790) and p65 (NCBI Gene ID: 5970), was inhibited, CD133 expression decreases (FIG. 1C). Promoter activity was observed in a promoter near CD133 ORF. Specifically, to measure the promoter activity, a CD133 ORF promoter region was cloned in a special vector expressing luciferase. Cells were simultaneously transfected with the luciferase vector and a *Renilla* plasmid vector for quantification. Twenty-four hours after transfection, the cells were treated with EGF for 14 hours, lysed with lysis buffer and centrifuged to obtain a supernatant, and then luciferase activity was measured using the Luminometer 20/20 (FIG. 1D). In a promoter which had been subjected to treatment with an NF-κB inhibitor and an NF-κB subunit-binding site, promoter activity was not observed (FIG. 1D). Taken together, it was confirmed that EGF activates NF-κB and regulates CD133 expression at the transcription level (FIG. 1A).

EXAMPLE 2

Identification of CD133 Role in Cancer Cells

The relationship between EGF and microvesicle and TNT formation was investigated by microscopic analysis. Specifically, after 14 hours of EGF treatment, cells were fixed with 4% paraformaldeyde and treated with WGA-488 and DAPI for 10 minutes to stain the cell membrane and nucleus. Fluorescence intensity was measured using an LSM700 Meta confocal microscope.

The results showed that, when a liver cancer cell line was treated with EGF, compared to a control, microvesicle and TNT formation increases between cells, and this phenomenon is decreased by treatment with the NF-κB inhibitor (WGA, cell membrane staining, FIG. 2A). In addition, in a CD133 expression-stable cell line, it was confirmed that microvesicles and TNT formation rates highly increase (FIG. 2B). Therefore, it was expected that microvesicle budding is closely related to the change in CD133 expression.

In addition, to bud microvesicles from the cell membrane, the regulation of activities of small GTPases such as ARF6, RhoA and Rac1 is known to be important, and thus an expression pattern of the gene according to the CD133 expression pattern was observed by small GTPase pull-down assay. Specifically, to measure Rac1 activity, after transfected with CD133, cells were harvested, and activity was measured using a Rac1 activation Assay kit. To measure RhoA activity, after CD133 transfection, cells were harvested, and activity was measured using a RhoA activation Assay kit. As a result, it was seen that, in the CD133 expression-stable cell line, Rac1 (NCBI Gene ID: 5879) activity decreases, RhoA (NCBI Gene ID: 387) activity increases, and thus the activity of the downstream signaling molecule Erk1/2 (NCBI Gene ID: 5595, 5594) increases (FIG. 2E). This result showed that a certain level of CD133 expression is essential for microvesicle formation, and particularly, small GTPase activity is regulated to promote microvesicle budding.

EXAMPLE 3

Analysis of Physiological Properties of Microvesicles Released From Cancer Cells Microvesicles were observed by microvesicle microscopic analysis. Specifically, microvesicles were isolated from the culture solution of CD133-transfected cells and stained with WGA-488, general cells were treated with the stained microvesicles, and after 12 hours, fluorescence intensity was measured using a LSM700 Meta confocal microscope.

It was observed that the microvesicles were released from various types of cancer cells, and contained CD133 (FIG. 3A). In addition, the CD133 (red)-containing microvesicles were isolated by centrifugation, and treated with WGA to stain the cell membrane. It was observed that, when the cell line was treated with the microvesicles, the microvesicles were transported to adjacent cells along with CD133 (FIG. 3B).

EXAMPLE 4

Identification of CD133 Role in Colon Cancer

Forty-eight hours after a HCT116 cell line was transfected with a shCD133 vector into which the shRNA sequence (5': GAGUCGGAAACUGGCAGAUAGCAAU-3': SEQ ID NO: 3) knocking down the CD133 expression was inserted to prepare a CD133 expression-inhibited cell line, selection was performed with a selection marker Zeocin. Afterward, single colonies were selected and subcultured, and subjected to Western blotting with wild-type HCT116 to verify CD133 knockdown. The used vector is a vector prepared by substituting a neomycin antibiotic region with Zeomycin in a pSilencer 2.1-U6 neo vector (https://www.thermofisher.com/kr/ko/home/life-science/dna-rnapurification-analysis/napamisc/vector-maps/psilencer-2-1-u6-hygro-vector-map.html).

To isolate microvesicles, the culture solutions of a CD133 normal expression cell line and a CD133 expression-inhibited cell line were collected, and then each cell culture solution was centrifuged at 20,000 g for 1 hour, thereby obtaining a supernatant. After discarding the supernatant, microvesicles were isolated.

From the isolated microvesicles, the amount and sizes of microvesicle budding were measured by a Malvern Nanosight Nanoparticle Tracking Analysis system.

KRAS (NCBI Gene ID: 3845) G13D is a well-known oncogenic protein, and usually found as a KRAS mutant in colon cancer. It was observed that, when CD133 expression was inhibited in a colon cancer cell line, KRAS G13D was not contained in the microvesicles (FIG. 4A). In addition, it was confirmed that CD133 expression is involved in determination of the amount and sizes (100 to 200 nm) of microvesicle budding (FIGS. 4B and 4C).

To observe the transport of KRAS G13D to adjacent cells, microvesicles were isolated from the CD133 expression-inhibited cell line and the general cell line and then normal cells were treated with the microvesicles. Specifically, for cell migration assay, microvesicle-recipient cells were cultured in an 8-μm pore insert, treated with microvesicles, and then after 48 hours, migrating cells counted. For invasion assay, an 8-μm pore insert was coated with Matrigel, and then recipient cells were incubated. Forty-eight hours after microvesicle treatment, cells migrating through the Matrigel were counted.

As a result, it was confirmed that, in normal cells treated with the microvesicles isolated from the general cell line, KRAS G13D is transported to adjacent cells via the microvesicles along with CD133, and the activation of KRAS downstream signaling molecules Akt (NCBI Gene ID: 207) and Erk1/2 increases (FIG. 4D). The microvesicle-mediated KRAS G13D transport induced increases in cell migration to (FIG. 4E) and invasiveness (FIG. 4F) of normal cells. Based on this result, it was able to be confirmed that CD133 regulates a microvesicle transport material, and plays a crucial role in microvesicle size and budding.

EXAMPLE 5

Confirmation of Induction of Anticancer Agent Resistance to Adjacent Cells by CD133-Containing Microvesicles in Colon Cancer While gefitinib is an anticancer material that inhibits EGFR activity and thus controls cancer cells, it was reported that, in certain types of cancer in which EGFR downstream signaling molecules including KRAS are activated, gefitinib efficacy was insignificant. It was inferred that the transport of KRAS G13D to adjacent cells by CD133-containing microvesicles is involved in resistance to such an EGFR-targeting agent.

Cells being cultured to confirm the above inference were incubated with gefitinib and the microvesicles for a suggested time, cell viability was analyzed using an EZ-cytox kit at specific time, and the absorbance was measured at 570 nm using a microplate reader, followed by calculating a cell growth rate. Twenty-four hours after treatment with the microvesicles and gefitinib, the cells were harvested, and then fixed with 95% cold ethanol. The fixed cells were treated with RNase and propidium iodide to stain DNA, and then the stained DNA was analyzed by FACS.

As a result, it was confirmed that, when treated along with gefitinib, microvesicles extracted from CD133 expression-inhibited colon cancer cells do not contribute to cell proliferation of adjacent recipient cells, but microvesicles extracted from CD133-expressing cells restore cell proliferation even when gefitinib is treated (FIGS. 5A and 5B). To demonstrate that such a change is caused by KRAS G13D transport by microvesicles, the change in KRAS downstream signaling molecules and target genes in microvesicle-recipient cells was observed. It was confirmed that the CD133-mediated KRAS G13D transport increases the activities of KRAS downstream signaling molecules FAK (NCBI Gene ID: 5747), Akt and Erk1/2 in the recipient cells (FIG. 5C). In addition, it was observed that mRNA expressions of KRAS target genes SERVIVIN (NCBI Gene ID: 332) and CCNB1 (NCBI Gene ID: 891) increase, anti-apoptotic mRNA (BCLXL, BCL2L2 (NCBI Gene ID: 598, 599)) increases, and pro-apoptotic mRNA (BIM (NCBI Gene ID: 10018)) decreases (FIG. 5D). This shows that the cell migration to and invasiveness of recipient cells receiving the oncogenic protein (KRAS G13D)-containing microvesicles increase, and thus the development of cancer is maintained after treatment with an anticancer agent. In conclusion, in colon cancer, CD133-containing microvesicles are involved in transport of the KRAS oncogenic protein to induce anticancer agent resistance to adjacent cells, thereby accelerating cancer development.

The invention claimed is:

1. A method of treating resistance to Gefitinib in colon cancer, the method comprising administering an inhibitor against a CD133 gene to a subject resistant to Gefitinib, wherein the inhibitor comprises an antisense oligonucleotide, siRNA, or shRNA against the CD133 gene, or a vector comprising the inhibitor.

* * * * *

SEQUENCE LISTING

```
<160> NUMBER OF SEQ ID NOS: 3

<210> SEQ ID NO 1
<211> LENGTH: 2598
<212> TYPE: DNA
<213> ORGANISM: Homo sapiens
```

<400> SEQUENCE: 1

```
atggccctcg tactcggctc cctgttgctg ctggggctgt gcgggaactc cttttcagga      60
gggcagcctt catccacaga tgctcctaag gcttggaatt atgaattgcc tgcaacaaat     120
tatgagaccc aagactccca taaagctgga cccattggca ttctctttga actagtgcat     180
atctttctct atgtggtaca gccgcgtgat ttcccagaag atactttgag aaaattctta     240
cagaaggcat atgaatccaa aattgattat gacaagccag aaactgtaat cttaggtcta     300
aagattgtct actatgaagc agggattatt ctatgctgtg tcctggggct gctgtttatt     360
attctgatgc ctctggtggg gtatttcttt tgtatgtgtc gttgctgtaa caatgtggt      420
ggagaaatgc accagcgaca aaggaaaat gggcccttcc tgaggaaatg ctttgcaatc      480
tccctgttgg tgatttgtat aataataagc attggcatct tctatggttt tgtggcaaat     540
caccaggtaa gaacccggat caaaaggagt cggaaactgg cagatagcaa tttcaaggac     600
ttgcgaactc tcttgaatga aactccagag caaatcaaat atatattggc ccagtacaac     660
actaccaagg acaaggcgtt cacagatctg aacagtatca attcagtgct aggaggcgga     720
attcttgacc gactgagacc caacatcatc cctgttcttg atgagattaa gtccatggca     780
acagcgatca aggagaccaa agaggcgttg agaacatga acagcacctt gaagagcttg     840
caccaacaaa gtacacagct agcagcagt ctgaccagcg tgaaaactag cctgcggtca      900
tctctcaatg accctctgtg cttggtgcat ccatcaagtg aaacctgcaa cagcatcaga     960
ttgtctctaa gccagctgaa tagcaaccct gaactgaggc agcttccacc cgtggatgca    1020
gaacttgaca acgttaataa cgttcttagg acagatttgg atggcctggt ccaacagggc    1080
tatcaatccc ttaatgatat acctgacaga gtacaacgcc aaaccacgac tgtcgtagca    1140
ggtatcaaaa gggtcttgaa ttccattggt tcagatatcg acaatgtaac tcagcgtctt    1200
cctattcagg atatactctc agcattctct gtttatgtta ataacactga agttacatc     1260
cacagaaatt tacctacatt ggaagagtat gattcatact ggtggctggg tggcctggtc    1320
atctgctctc tgctgaccct catcgtgatt ttttactacc tgggcttact gtgtggcgtg    1380
tgcggctatg acaggcatgc caccccgacc acccgaggct gtgtctccaa caccggaggc    1440
gtcttcctca tggttggagt tggattaagt ttcctctttt gctggatatt gatgatcatt    1500
gtggttctta cctttgtctt tggtgcaaat gtggaaaaac tgatctgtga accttacacg    1560
agcaaggaat tattccgggt tttggataca ccctacttac taaatgaaga ctgggaatac    1620
tatctctctg ggaagctatt taataaatca aaaatgaagc tcactttga acaagtttac    1680
agtgactgca aaaaaaatag aggcacttac ggcactcttc acctgcagaa cagcttcaat    1740
atcagtgaac atctcaacat taatgagcat actggaagca taagcagtga attggaaagt    1800
ctgaaggtaa atcttaatat ctttctgttg ggtgcagcag gaagaaaaaa ccttcaggat    1860
tttgctgctt gtgaaataga cagaatgaat tatgacagct acttggctca gactggtaaa    1920
tcccccgcag gagtgaatct tttatcattt gcatatgatc tagaagcaaa agcaaacagt    1980
ttgcccccag gaaatttgag gaactccctg aaaagagatg cacaaactat taaaacaatt    2040
caccagcaac gagtccttcc tatagaacaa tcactgagca ctctatacca aagcgtcaag    2100
atacttcaac gcacagggaa tggattgttg agagagtaa ctaggattct agcttctctg     2160
gattttgctc agaacttcat cacaaacaat acttcctctg ttattattga ggaaactaag    2220
aagtatggga gaacaataat aggatatttt gaacattatc tgcagtggat cgagttctct    2280
```

```
atcagtgaga aagtggcatc gtgcaaacct gtggccaccg ctctagatac tgctgttgat    2340
gtctttctgt gtagctacat tatcgacccc ttgaatttgt tttggtttgg cataggaaaa    2400
gctactgtat ttttacttcc ggctctaatt tttgcggtaa aactggctaa gtactatcgt    2460
cgaatggatt cggaggacgt gtacgatgat gttgaaacta tacccatgaa aaatatggaa    2520
aatggtaata atggttatca taaagatcat gtatatggta ttcacaatcc tgttatgaca    2580
agcccatcac aacattga                                                  2598
```

<210> SEQ ID NO 2
<211> LENGTH: 865
<212> TYPE: PRT
<213> ORGANISM: Homo sapiens

<400> SEQUENCE: 2

```
Met Ala Leu Val Leu Gly Ser Leu Leu Leu Gly Leu Cys Gly Asn
1               5                   10                  15

Ser Phe Ser Gly Gly Gln Pro Ser Ser Thr Asp Ala Pro Lys Ala Trp
            20                  25                  30

Asn Tyr Glu Leu Pro Ala Thr Asn Tyr Glu Thr Gln Asp Ser His Lys
        35                  40                  45

Ala Gly Pro Ile Gly Ile Leu Phe Glu Leu Val His Ile Phe Leu Tyr
    50                  55                  60

Val Val Gln Pro Arg Asp Phe Pro Glu Asp Thr Leu Arg Lys Phe Leu
65                  70                  75                  80

Gln Lys Ala Tyr Glu Ser Lys Ile Asp Tyr Asp Lys Pro Glu Thr Val
                85                  90                  95

Ile Leu Gly Leu Lys Ile Val Tyr Tyr Glu Ala Gly Ile Ile Leu Cys
            100                 105                 110

Cys Val Leu Gly Leu Leu Phe Ile Ile Leu Met Pro Leu Val Gly Tyr
        115                 120                 125

Phe Phe Cys Met Cys Arg Cys Cys Asn Lys Cys Gly Gly Glu Met His
    130                 135                 140

Gln Arg Gln Lys Glu Asn Gly Pro Phe Leu Arg Lys Cys Phe Ala Ile
145                 150                 155                 160

Ser Leu Leu Val Ile Cys Ile Ile Ile Ser Ile Gly Ile Phe Tyr Gly
                165                 170                 175

Phe Val Ala Asn His Gln Val Arg Thr Arg Ile Lys Arg Ser Arg Lys
            180                 185                 190

Leu Ala Asp Ser Asn Phe Lys Asp Leu Arg Thr Leu Leu Asn Glu Thr
        195                 200                 205

Pro Glu Gln Ile Lys Tyr Ile Leu Ala Gln Tyr Asn Thr Thr Lys Asp
    210                 215                 220

Lys Ala Phe Thr Asp Leu Asn Ser Ile Asn Ser Val Leu Gly Gly Gly
225                 230                 235                 240

Ile Leu Asp Arg Leu Arg Pro Asn Ile Ile Pro Val Leu Asp Glu Ile
                245                 250                 255

Lys Ser Met Ala Thr Ala Ile Lys Glu Thr Lys Glu Ala Leu Glu Asn
            260                 265                 270

Met Asn Ser Thr Leu Lys Ser Leu His Gln Gln Ser Thr Gln Leu Ser
        275                 280                 285

Ser Ser Leu Thr Ser Val Lys Thr Ser Leu Arg Ser Ser Leu Asn Asp
    290                 295                 300

Pro Leu Cys Leu Val His Pro Ser Ser Glu Thr Cys Asn Ser Ile Arg
305                 310                 315                 320
```

```
Leu Ser Leu Ser Gln Leu Asn Ser Asn Pro Glu Leu Arg Gln Leu Pro
                325                 330                 335

Pro Val Asp Ala Glu Leu Asp Asn Val Asn Asn Val Leu Arg Thr Asp
            340                 345                 350

Leu Asp Gly Leu Val Gln Gln Gly Tyr Gln Ser Leu Asn Asp Ile Pro
                355                 360                 365

Asp Arg Val Gln Arg Gln Thr Thr Thr Val Val Ala Gly Ile Lys Arg
        370                 375                 380

Val Leu Asn Ser Ile Gly Ser Asp Ile Asp Asn Val Thr Gln Arg Leu
385                 390                 395                 400

Pro Ile Gln Asp Ile Leu Ser Ala Phe Ser Val Tyr Val Asn Asn Thr
                405                 410                 415

Glu Ser Tyr Ile His Arg Asn Leu Pro Thr Leu Glu Glu Tyr Asp Ser
                420                 425                 430

Tyr Trp Trp Leu Gly Gly Leu Val Ile Cys Ser Leu Leu Thr Leu Ile
                435                 440                 445

Val Ile Phe Tyr Tyr Leu Gly Leu Leu Cys Gly Val Cys Gly Tyr Asp
        450                 455                 460

Arg His Ala Thr Pro Thr Thr Arg Gly Cys Val Ser Asn Thr Gly Gly
465                 470                 475                 480

Val Phe Leu Met Val Gly Val Gly Leu Ser Phe Leu Phe Cys Trp Ile
                485                 490                 495

Leu Met Ile Ile Val Val Leu Thr Phe Val Phe Gly Ala Asn Val Glu
                500                 505                 510

Lys Leu Ile Cys Glu Pro Tyr Thr Ser Lys Glu Leu Phe Arg Val Leu
            515                 520                 525

Asp Thr Pro Tyr Leu Leu Asn Glu Asp Trp Gly Tyr Tyr Leu Ser Gly
            530                 535                 540

Lys Leu Phe Asn Lys Ser Lys Met Lys Leu Thr Phe Glu Gln Val Tyr
545                 550                 555                 560

Ser Asp Cys Lys Lys Asn Arg Gly Thr Tyr Gly Thr Leu His Leu Gln
                565                 570                 575

Asn Ser Phe Asn Ile Ser Glu His Leu Asn Ile Asn Glu His Thr Gly
                580                 585                 590

Ser Ile Ser Ser Glu Leu Glu Ser Leu Lys Val Asn Leu Asn Ile Phe
            595                 600                 605

Leu Leu Gly Ala Ala Gly Arg Lys Asn Leu Gln Asp Phe Ala Ala Cys
        610                 615                 620

Gly Ile Asp Arg Met Asn Tyr Asp Ser Tyr Leu Ala Gln Thr Gly Lys
625                 630                 635                 640

Ser Pro Ala Gly Val Asn Leu Leu Ser Phe Ala Tyr Asp Leu Glu Ala
                645                 650                 655

Lys Ala Asn Ser Leu Pro Pro Gly Asn Leu Arg Asn Ser Leu Lys Arg
                660                 665                 670

Asp Ala Gln Thr Ile Lys Thr Ile His Gln Gln Arg Val Leu Pro Ile
            675                 680                 685

Glu Gln Ser Leu Ser Thr Leu Tyr Gln Ser Val Lys Ile Leu Gln Arg
        690                 695                 700

Thr Gly Asn Gly Leu Leu Glu Arg Val Thr Arg Ile Leu Ala Ser Leu
705                 710                 715                 720

Asp Phe Ala Gln Asn Phe Ile Thr Asn Asn Thr Ser Ser Val Ile Ile
                725                 730                 735
```

```
Glu Glu Thr Lys Lys Tyr Gly Arg Thr Ile Ile Gly Tyr Phe Glu His
            740                 745                 750

Tyr Leu Gln Trp Ile Glu Phe Ser Ile Ser Glu Lys Val Ala Ser Cys
            755                 760                 765

Lys Pro Val Ala Thr Ala Leu Asp Thr Ala Val Asp Val Phe Leu Cys
            770                 775                 780

Ser Tyr Ile Ile Asp Pro Leu Asn Leu Phe Trp Phe Gly Ile Gly Lys
785                 790                 795                 800

Ala Thr Val Phe Leu Leu Pro Ala Leu Ile Phe Ala Val Lys Leu Ala
                805                 810                 815

Lys Tyr Tyr Arg Arg Met Asp Ser Glu Asp Val Tyr Asp Asp Val Glu
            820                 825                 830

Thr Ile Pro Met Lys Asn Met Glu Asn Gly Asn Asn Gly Tyr His Lys
            835                 840                 845

Asp His Val Tyr Gly Ile His Asn Pro Val Met Thr Ser Pro Ser Gln
            850                 855                 860

His
865

<210> SEQ ID NO 3
<211> LENGTH: 25
<212> TYPE: RNA
<213> ORGANISM: Artificial Sequence
<220> FEATURE:
<223> OTHER INFORMATION: CD133 inhibitor shRNA

<400> SEQUENCE: 3
gagucggaaa cuggcagaua gcaau                                          25
```